United States Patent [19]

Chiba et al.

[11] Patent Number: 5,269,174
[45] Date of Patent: Dec. 14, 1993

[54] METHOD AND APPARATUS FOR EXAMINING AND DETERMINING THE VISCOSITY OF A LIQUID IN A CONTAINER

[75] Inventors: Yuho Chiba; Takao Tomita, both of Higashimurayama, Japan

[73] Assignee: Meiji Milk Products Co., Ltd., Tokyo, Japan

[21] Appl. No.: 919,322

[22] Filed: Jul. 27, 1992

Related U.S. Application Data

[63] Continuation of Ser. No. 578,005, Sep. 4, 1990, Pat. No. 5,187,975.

[30] Foreign Application Priority Data

Dec. 26, 1989 [JP] Japan .................... 1-336908

[51] Int. Cl.$^5$ .................................... G01N 11/02
[52] U.S. Cl. ............................................ 73/54.01
[58] Field of Search ........................... 73/54.01, 54.02

[56] References Cited

U.S. PATENT DOCUMENTS

| 3,824,841 | 8/1974 | Bull | 73/61.4 |
| 4,848,900 | 7/1989 | Kuo et al. | 73/61.4 |

FOREIGN PATENT DOCUMENTS

| 0269815 | 6/1988 | European Pat. Off. |  |
| 246639 | 10/1988 | Japan | 73/61.4 |
| 2192463 | 1/1988 | United Kingdom . |  |
| 2192987 | 1/1988 | United Kingdom . |  |

OTHER PUBLICATIONS

Azimov, A., "Soviet Inventions Illustrated", Week 8843 88-306354/43 (1988).

*Primary Examiner*—Herzon E. Williams
*Assistant Examiner*—Raymond Y. Mah
*Attorney, Agent, or Firm*—Wenderoth, Lind & Ponack

[57] ABSTRACT

This invention presents a method and an apparatus for examining and determining the viscosity of a liquid sealed in a container by applying a centrifugal force to the container, detecting a change in the surface form of said liquid by the means of a sensor, and measuring either a lapse of time from the application of centrifugal force to the time when the output voltage of the sensor reaches a predetermined level or a voltage output of the sensor upon a predetermined lapse of time from the application of a centrifugal force, thereby examining and determining the viscosity of the liquid to find out whether there is any quality change in the liquid without destroying the container.

4 Claims, 3 Drawing Sheets

METHOD AND APPARATUS FOR EXAMINING AND DETERMINING THE VISCOSITY OF A LIQUID IN A CONTAINER

This is a Rule 60 Continuation of Ser. No. 07/578,005 filed Sep. 4, 1990, now U.S. Pat. No. 5,187,975

FIELD OF THE INVENTION

This invention relates to a method and an apparatus for examining and determining the viscosity of a liquid in a container to determine whether there is any quality change in the liquid sealed in the container without destroying or opening said container.

PRIOR ART

Conventionally, it has not been possible to determine whether a liquid-form foodstuff sealed in a container has had its viscosity changed by germs or bacteria-caused deficiency, without opening the container.

It has been known to determine such a viscosity change in liquids other than foodstuffs from a torque difference sensed and detected by shaking their containers.

Among the thus-known conventional methods, the former, requiring containers to be opened, is not applicable to such objects as commercial products and goods which can not be opened.

Determining a viscosity change from a torque difference as employed in the latter method, meanwhile, is not practically effective when such a torque difference is small.

SUMMARY OF THE INVENTION

To overcome the above-described problems inherent in the conventional methods, the present invention employs a centrifugal force which is applied to a liquid to be examined to cause a change in the form of its surface, in order to make it possible to recognize relatively a small viscosity change with accuracy by detecting the said centrifugal force-caused surface change with a sensor.

More particularly, the present invention provides a method for examining and determining the viscosity of a liquid in a container comprising the steps of applying a centrifugal force to a liquid sealed in a light permeable container, detecting a change in the surface form of said liquid by the means of a sensor, and measuring a lapse of time from the application of centrifugal force to the detection of a predetermined level of an output voltage of said sensor. The present invention also provides a method for examining and determining the viscosity of a liquid in a container comprising the steps of applying a centrifugal force to a liquid sealed in a light permeable container, detecting a change in the surface form of said liquid by the means of a sensor, and measuring the voltage output of the said sensor upon a predetermined lapse of time from the application of the centrifugal force. In the above, said centrifugal force is caused and applied to the container by rotating the container at a speed of 300 to 1,500 rpm. Further, the present invention provides an apparatus for examining and determining the viscosity of a liquid in a container comprising, container holder linked to a rotation force input, sensor holding plate shiftable in its vertical direction provided around said container holder, level-detection photoelectric tube sensor and an analog output type photoelectric sensor both set on said sensor holding plate, and data processing device connected through its input to the output of said analog output type photoelectric sensor.

The level-detection photoelectric tube sensor is provided on the sensor holding plate on which the analog output type photoelectric sensor is also provided, and shifts in association with the sensor holding plate to adjust the level of analog output type photoelectric sensor to the level of surface of the liquid to be examined at every time before the rotation of the container holder is started.

When a centrifugal force is applied to a liquid sealed in a container to be examined according to the present invention, the surface of the liquid takes on a recessed arcular form. If a change in the liquid surface form is detected by the analog output type photoelectric sensor, an increase in the thickness of the liquid surface in its recessed arcular cross section shows, for instance, a voltage drop. A lapse of time measured from the application of a centrifugal force to the detection of a predetermined voltage drop, accordingly, changes in correspondence to a viscosity change in the liquid. Likewise, the output voltage level of the analog output type photoelectric sensor measured upon the constant time after the application of a centrifugal force changes in correspondence to a liquid viscosity change.

In their viscosity changes resulting from bacteria-caused deficiency, foodstuffs are divided into two opposite groups: one shows an increase and the other a decrease. However, the same device can be used to examine and determine the viscosity of a particular liquid-form foodstuff irrespective of a fluctuation of its viscosity once standard data based on its normal viscosity level is inputted. Viscosity changes in a same liquid-form foodstuff resulting from its bacteria-caused deficiency show such a particular relationship between a levels of an output voltage from the analog output type photoelectric sensor and a lapse of time from the application of centrifugal force to said liquid-form foodstuff sealed in a container as the relationship which represented in a similar figure graph in accordance with their respective levels of viscosity (FIG. 3).

The graph presented as FIG. 3 shows the relationship between output voltage levels of the analog output type photoelectric sensor and a lapse of time from the application of centrifugal force in the case of a same liquid-form foodstuff varying in deficiency-caused viscosity. In the drawing with a vertical axis showing output voltage levels and a horizontal axis showing a lapse of time, A and C represent high and low levels of viscosity, respectively, and B a medium level therebetween.

Therefore, it can be easily detected whether there is any abnormal viscosity in a liquid-form foodstuff by using either of the following methods; In one ease the output voltage level of the analog output type photoelectric sensor is used as a criterion and the lapse of time from the application of centrifugal force to a normal liquid-form foodstuff sealed in a container to the detection of a predetermined level of an output voltage of said sensor is measured. And said measured lapse of time is retained as a standard data. At the time when the similar liquid-form foodstuffs sealed in other containers are to be examined, the lapse of time from the application of centrifugal force to the examined liquid-form foodstuff sealed in other container to the detection of a predetermined level of an output voltage of said sensor, which is identical with the predetermined level of an output voltage of said sensor used for measuring the before mentioned standard data, is measured in the same manner. This measured lapse of time is then compared against the before mentioned standard data for detecting whether there is any abnormal viscosity in said examined liquid-form foodstuff.

In this case, the lapse of time from the application of the centrifugal force to the liquid-form foodstuff sealed in a container is used as a criterion and the output voltage of the analog output type photoelectric sensor upon a predetermined lapse of time from the application of centrifugal force to a normal liquid-form foodstuff sealed in a container is measured. Said measured output voltage is retained as a standard data.

At the time when the similar liquid-form foodstuffs sealed in other containers are to be examined, the output voltage of the sensor upon a predetermined lapse of time from the application of centrifugal force, which is identical with the lapse of time used for measuring the before mentioned standard data, is measured in the same manner. This measured output voltage of the sensor is then compared against the before mentioned standard data for detecting whether there is any abnormal viscosity in said examined liquid-form foodstuff.

The above-described predetermined voltage based on an output voltage as its criterion is a value which most conspicuously shows a difference in the graph presenting relationship between output voltage levels of the analog output type photoelectric sensor and a lapse of time after the application of a centrifugal force, and obtained by the tests with respect to the liquid-form foodstuffs which are examined and compared about their viscosity changes. Generally, an input voltage for an analogue/digital convertor IC is set within a range of DC±10 V. The range of an analogue/digital convertor IC input voltage in the embodiment of the present invention was from DC 0 V to 10 V and its maximum value in the graph presented as FIG. 3 is presented as 10 V.

The above-described predetermined lapse of time used as a criterion, is the time from the application of a centrifugal force to a liquid-form foodstuff to the time when the liquid-form foodstuff changes in its surface form, which varies, depending on its viscosity difference. Normally, such a change in the surface of a liquid-form to foodstuff is completed within a few seconds from the start or suspension of its rotation.

Though depending on the viscosity of liquid-form foodstuffs, to be examined, a centrifugal force as described in the above is not sufficient enough to, when the rotation of the container contains foodstuff to be examined is slow at a speed of less than 300 rpm, cause the liquid-form foodstuff to be pressed to and rise on the inner wall portion of its container. On the other hand, when the rotation is faster than 1,500 rpm conversely, such a centrifugal force causes the liquid-form foodstuff to be examined to rise on the inner wall portion of its container too quickly and form rough surface, making the resultant data unreliable. It is desirable to, therefore, cause and apply the centrifugal force to the container which contains a liquid-form foodstuff to be examined by rotating the container at a speed of 300 to 1,500 rpm.

As described in the above, the present invention has advantage of making it possible to examine a liquid sealed in a container to determine its viscosity change without destroying the container thereof. The invention is thus effective to examine a liquid-form foodstuff well sealed in a container whether there is any viscosity change in the foodstuff due to bacteria-caused deficiency, without destroying said container.

If an output from a data processing device is connected to an input of control system for a container-conveying device, inferior quality goods such as liquid-form foodstuffs having abnormal viscosity as a result of bacteria-caused deficiency is sealed in a container can be removed or discarded automatically.

PREFERABLE EMBODIMENT OF THE INVENTION

Embodiment 1

Figure 1:
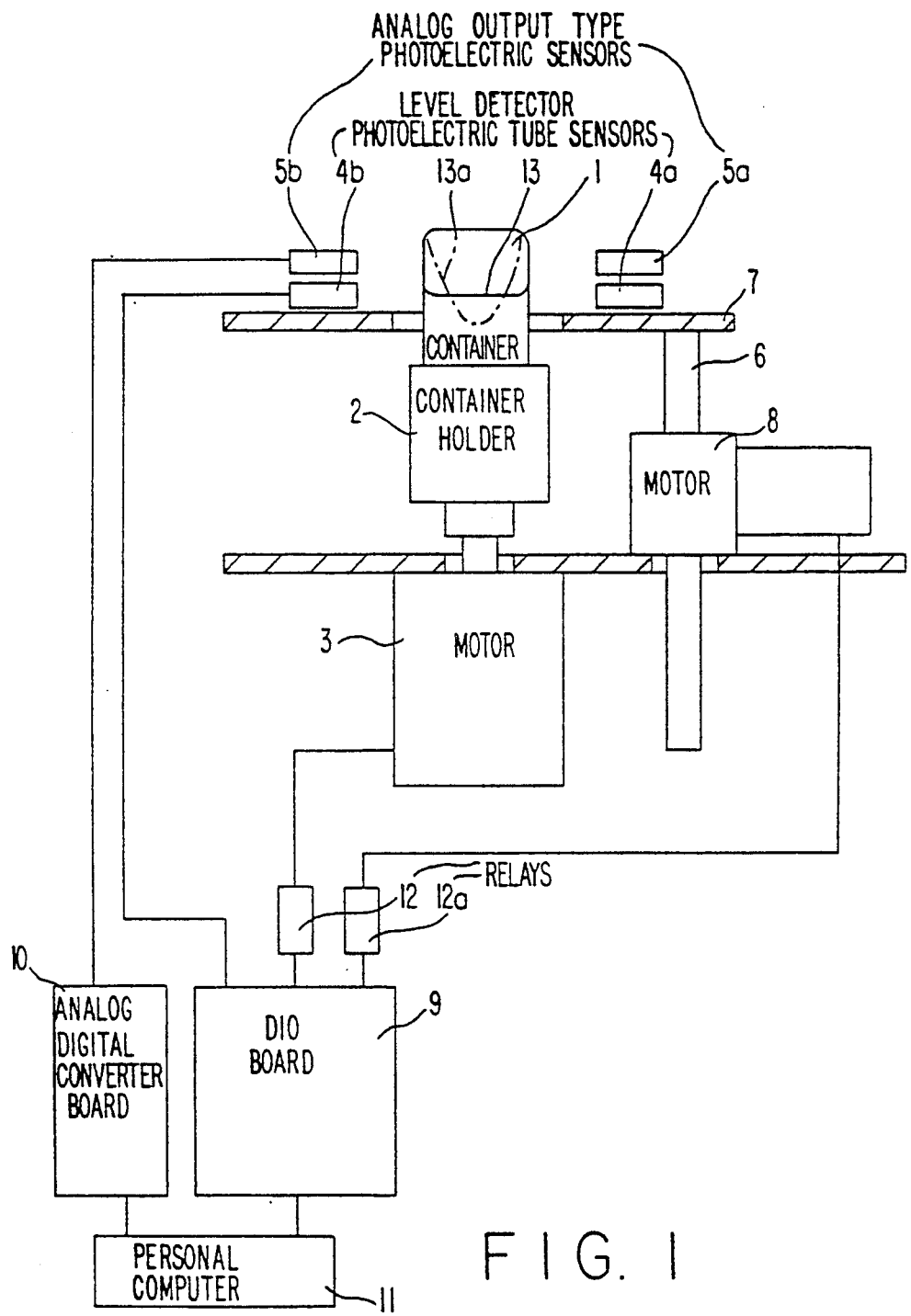
FIG. 1 is a front view of an apparatus according to the present invention, partially shown in block diagram.

The invention is described hereinbelow along with its embodiments.

The invention was embodied with 50 cc of processed milk filled in a permeable polyethylene bottle having 5 cm diameter, 7 cm in height and 0.7 mm in thickness.

In the liquid viscosity examination carried out in accordance with the invention, the fresh processed milk immediately after its production was compared with the same implanted with unspecified strains of bacteria and left in a room-temperature atmosphere for four to five days and for two weeks. Presented here below were viscosity data of samples which were obtained from the before mentioned three cases and were used for this liquid viscosity examination.

Viscosity: 1.4 CP (viscosity lowered)
Viscosity: 1.9 CP (viscosity unchanged)
Viscosity: 2.4 CP (viscosity heightened)
Viscosity: 3.5 CP (viscosity heightened)

Viscosity 1.9 CP (viscosity unchanged) presented in the above is a measured level of viscosity of fresh processed milk in a normal state immediately after its production.

In the viscosity examination, said sample was filled in a container holder 2 and rotated at a speed of 500 rpm. Then, a lapse of time was measured from the start of rotation of container holder 2 to the state at which the output voltage from an analog output type photoelectric sensor 5 reaches at 5 V. Also the output voltage of the analog output type photoelectric sensor 5 was measured 1.5 seconds after the start of the container rotation.

The time required for the output voltage of the analog output type photoelectric sensor 5 to reach a level of 5 V and the voltage output of the sensor at 1.5 seconds after the start of the container rotation both turned out to be shorter and lower when the viscosity is higher than the viscosity stays unchanged, proving that a liquid-form foodstuff with its viscosity changed as a result of bacteria-caused deficiency can be detected.

The measurement of viscosity, the measurement of a lapse of time from the start of the container rotation to the time when the output voltage from the sensor reaches at 5 V and the measurement of a sensor output voltage upon 1.5 seconds after the start of the container rotation were carried out at a temperature of 20 degrees Centigrade.

The lapse of time from the start of the container rotation to the time when the output voltage from an analog output type photoelectric sensor 5 reaches at 5 V is as shown in Table 1.

TABLE 1

| Viscosity (CP) | Lapse of Time (Second) |
|---|---|
| 1.4 | 2.21 |
| 1.9 | 1.73 |
| 2.4 | 1.58 |
| 3.5 | 1.44 |

An output voltage from the analog output type photoelectric sensor 5 upon 1.5 seconds after the container rotation is as shown in Table 2.

TABLE 2

| Viscosity (CP) | Output Voltage (V) |
|---|---|
| 1.4 | 6.8 |
| 1.9 | 5.8 |
| 2.4 | 5.3 |
| 3.5 | 4.7 |

It was proved through the above measurement that viscosity can be determined to a difference of viscosity of 1 CP. In other words, viscosity can be measured in a unit of 1 CP to determine whether there is any abnormal viscosity in a liquid-form foodstuff.

Embodiment 2

In this embodiment, 50 cc of condensed milk was filled in a permeable polyethylene bottle having 5 cm diameter, 7 cm in height and 0.7 mm in thickness.

In the liquid viscosity examination carried out in accordance with the invention, the fresh condensed milk immediately after its production was compared with the same implated with unspecified strains of bacteria left in a room-temperature atmosphere for four to five days and for two weeks. Presented hereinbelow were viscosity data of samples which were obtained from the before mentioned three cases and were used for this liquid viscosity examination.

Viscosity: 4 CP (viscosity lowered)
Viscosity: 5 CP (viscosity unchanged)
Viscosity: 9.9 CP (viscosity heightened)
Viscosity: 20 CP (viscosity heightened)

Viscosity 5 CP (viscosity unchanged) presented in the above is a measured level of viscosity of fresh condensed milk in a normal state immediately after its production.

In the viscosity examination, said sample was filled in the container holder 2 and rotated at a speed of 500 rpm. Then, a lapse of time was measured from the start of the rotation of container holder 2 to the state at which the output voltage from an analog output type photoelectric sensor 5 reaches at 5 V. Also the output voltage of the analog output type photoelectric sensor 5 was measured at 1.3 seconds after the start of the container rotation.

The time required for the output voltage of the analog output type photoelectric sensor 5 to reach a level of 5 V and the voltage of the sensor at 1.3 seconds after the start of the container rotation both turned out to be shorter and lower when the viscosity is higher than when the viscosity stays unchanged, proving that a liquid-form foodstuff with its viscosity changed as a result of bacteria-caused deficiency can be detected.

The measurement of viscosity, the measurement of a lapse of time from the start of the container rotation to the time when the output voltage from the sensor reaches at 5 V and the measurement of a sensor output voltage at 1.3 seconds after the start of the container rotation were carried out at a temperature of 20 degrees Centigrade.

The lapse of time from the start of the container rotation to the time when the output voltage from an analog output type photoelectric sensor 5 reaches at 5 V is as shown in Table 3.

TABLE 3

| Viscosity (CP) | Lapse of Time (Second) |
|---|---|
| 4.0 | 1.33 |
| 5.0 | 1.25 |
| 9.9 | 1.13 |
| 20.0 | 1.06 |

The output voltage from the analog output type photoelectric sensor 5 at 1.3 seconds after the start of the container rotation is as shown in Table 4.

TABLE 4

| Viscosity (CP) | Output Voltage (V) |
|---|---|
| 4.0 | 5.0 |
| 5.0 | 4.5 |
| 9.9 | 3.8 |
| 20.0 | 3.0 |

It was proved through the above measurement that viscosity can be determined to a difference of 1 CP. In other words, viscosity can be measured in a unit of 1 CP to determine whether there is any abnormal viscosity in a liquid-form foodstaff.

Embodiment 3

A preferred embodiment of the present invention is described hereinafter along with FIGS. 1 and 2.

A container holder 2 is linked with the shaft of a motor 3 and capable to contain a container 1. A sensor holding plate 7 horizontally held by a support rod 6 is provided outside around the container 1. Said support rod 6 is linked with the output shaft of a motor 8 for driving it in its vertical direction.

Figure 2:
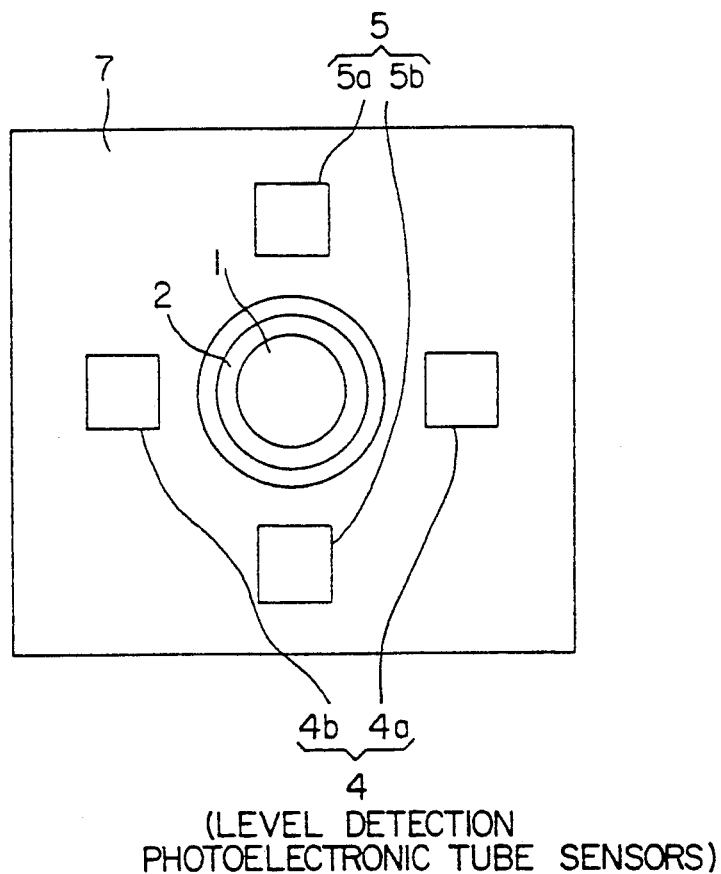
FIG. 2 is a partial plane view of the same.

A sensor positioned on said sensor holding plate 7 comprises a level-detection photoelectric tube sensor 4 and an analog output type photoelectric sensor 5, arranged at the right angles each other on the plate 7, as shown in FIG. 2. An output from a light reception device 4b of the level-detection photoelectric tube sensor 4 is connected to a DIO board 9 and linked with a circuit of the motor 8. Meanwhile, an output from a light reception device 5b of the analog output type photoelectric sensor 5 is connected to an analogue/digital converter board 10, and both said DIO board 9 and analogue/digital converter board 10 are both connected to a personal computer 11. Designated by numerals 12 and 12a in the drawings are relays. Thus constructed, the personal computer 11 through its processing can not only control the motors 3 and 8 but also execute the disposal and removal of deficient goods containing a liquid-form foodstuff having abnormal viscosity by connecting the output of personal computer 11 to a transfer line for goods and products.

With the above structure, the motor 8, when rotated, shifts the support rod 6 up and down in its vertical direction to adjust the level of the level-detection photoelectric sensor 4 to the liquid surface 13 in the container 1. When the motor 3 is started, the container holder 2 is rotated to rotate the container 1, the liquid surface in the container 1 is formed into a recessed arcular shape 13a under the influence of a centrifugal force. Light emitted from a light projector 5a of an analog output type photoelectric sensor 5 passes through the liquid and the light permeable container reaches a light reception device 5b. The amount of light received at said light reception device 5b is measured by an analogue/digital converter board 10 in its converted voltage. The lapse of time required for the output voltage of the analog output type photoelectric sensor 5 to reach its predetermined level after the start of the rotation of container 1 and the output voltage of the sensor 5 after a predetermined lapse of time from the start of the rotation of container 1 are recorded by a personal computer 11.

Figure 3:
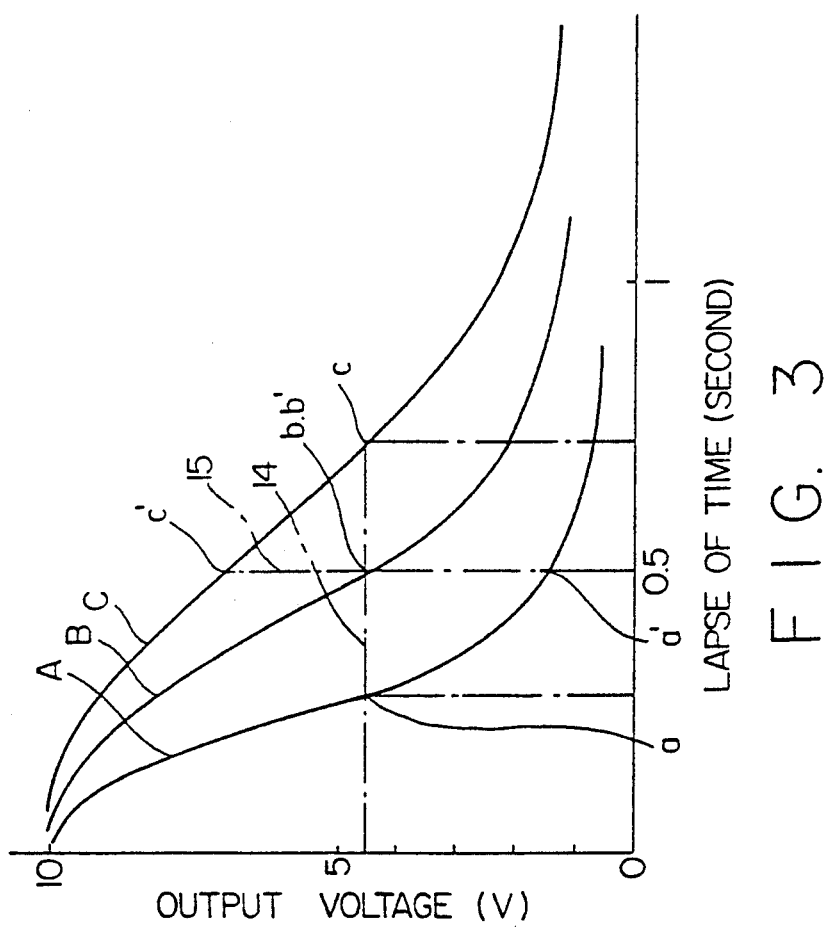
FIG. 3 is a graph presenting results of the viscosity test according to the present invention.

The rising speed of the liquid surface, depending on viscosity of a liquid to be measured, is represented as shown by curves A, B and C in FIG. 3. In FIG. 3, the curve A represents high viscosity, C represents low viscosity and B represents medium-level viscosity therebetween.

From FIG. 3, the horizontal line 14 representing the output voltage at a level of 4.5 V crosses with the curves A, B and C at points represented by a, b and c respectively, it is self-explained that the lapse of time required for the output voltage to reach at a level of 4.5 V after the start of the container rotation is, in order, 0.3 seconds, 0.5 seconds and 0.7 seconds with respect to the respective curves A, B and C. The vertical line 15 representing the lapse of time upon 0.5 seconds after the start of the container rotation crosses with the curves A, B and C at the points a', b' and c', the output voltage upon 0.5 seconds after the start of the container rotation is, in order, 1.2 V, 4.5 V and 6.9 V, respectively. Thus, it has been proved and become clear that the measurements of the output voltage and lapse of time have particular relationships in common thereto, respectively. As clear from the above, it is possible to determine the viscosity of a liquid in a container either by measuring the lapse of time from the start of the container rotation to the time when the output voltage of the analog output type photoelectric sensor reaches its predetermined level from its base level or by measuring an output voltage level of the sensor upon a predetermined lapse of time after the start of the container rotation.

What is claimed is:

1. A method for the examination of a package comprising a light permeable container and fluid content to determine whether there has been any unacceptable alteration of the viscosity of the fluid content, the method comprising the steps of:
   a. setting the package containing the fluid content in its unaltered state on a rotatable container holder;
   b. detecting a surface level of the fluid content by a level-detection photoelectric tube sensor and adjusting a level of an analog output type photoelectric sensor which is arranged at right angles to the level-detection photoelectric tube sensor to the same level as the surface of the fluid content;
   c. rotating the container holder and applying a centrifugal force to the package containing the fluid content for causing a change in surface form of the fluid content into a recessed arcuate form;
   d. detecting a change in surface form of the fluid content by the analog output type photoelectric sensor;
   e. converting the detected change in surface form of the fluid content into an alteration of output voltage;
   f. detecting the alteration of output voltage and a lapse of time measured from the beginning of the rotation of the container holder as a reference value;
   g. repeating the said steps a. to f. for other packages each containing the same material to determine whether there has been any unacceptable alteration of the viscosity of the fluid content, and obtaining the lapse of time measured from the beginning of the rotation of the container holder to the detection of predetermined level of output voltage for each of other packages;
   h. comparing each such specific value with the lapse of time measured from the beginning of the rotation of the container holder to the detection of predetermined level of the output voltage in the case of said reference value; and
   i. determining from said differences whether there is any unacceptable alteration of the viscosity of the fluid content in each of the said other packages.

2. The method as claimed in claim 1, wherein said centrifugal force is applied to the package by rotating the container holder at a speed of 300 to 1,500 rpm.

3. A method for enabling examination of a package comprising a light permeable container and fluid content to determine whether there has been any unacceptable alteration of the viscosity of the fluid content, the method comprising the steps of:
   a. setting the package containing the fluid content in its unaltered state on a rotatable container holder;
   b. detecting a surface level of the fluid content by a level-detection photoelectric tube sensor and adjusting a level of an analog output type photoelectric sensor which is arranged at right angles to the level-detection photoelectric tube sensor to the same level as the surface of the fluid content;
   c. rotating the container holder and applying a centrifugal force to the package containing the fluid content for causing a change in surface form of the fluid content into a recessed arcuate form;
   d. detecting a change in surface form of the fluid content by the analog output type photoelectric sensor;
   e. converting the detected change in surface form of the fluid content into an alteration of output voltage;
   f. detecting the alteration of output voltage and lapse of time measured from the beginning of the rotation of the container holder as a reference value;
   g. repeating the said steps a. to f. for other packages each containing the same material to determine whether there has been any unacceptable alteration of the viscosity of the fluid content, and obtaining the level of the output voltage when the predetermined time expires, from the beginning of the rotation of the container holder for each of the other packages;
   h. comparing each such specific value with the level of the output voltage detected when the predetermined time expires, from the beginning of the rotation of the container holder in the case of said reference value; and
   i. determining from said differences whether there is any unacceptable alteration of the viscosity of the fluid content in each of the said other packages.

4. The method as claimed in claim 3, wherein said centrifugal force is caused and applied to the package by rotating the container holder at a speed of 300 to 1,500 rpm.

* * * * *